United States Patent
Hacke et al.

(10) Patent No.: US 8,622,058 B2
(45) Date of Patent: Jan. 7, 2014

(54) MEDICAL AIR TUBING CONNECTION SYSTEM

(75) Inventors: Gerhard A. Hacke, Erin (CA); Cornel C. Hacke, Guelph (CA)

(73) Assignee: Respan Products, Inc., Erin, Ontario (CA)

( * ) Notice: Subject to any disclaimer, the term of this patent is extended or adjusted under 35 U.S.C. 154(b) by 815 days.

(21) Appl. No.: 12/709,661

(22) Filed: Feb. 22, 2010

(65) Prior Publication Data

US 2011/0203582 A1  Aug. 25, 2011

(51) Int. Cl.
- *A62B 9/02* (2006.01)
- *A62B 7/00* (2006.01)
- *F16K 37/00* (2006.01)
- *F17D 3/00* (2006.01)

(52) U.S. Cl.
USPC ............ 128/205.24; 128/202.27; 128/200.24; 128/205.23; 137/551; 137/559

(58) Field of Classification Search
USPC ........................... 128/200.24, 202.27, 205.24
See application file for complete search history.

(56) References Cited

U.S. PATENT DOCUMENTS

| | | | |
|---|---|---|---|
| 3,170,667 A | 2/1965 | Szohatzky | |
| 3,459,177 A | 8/1969 | Deuschle | |
| 3,544,257 A * | 12/1970 | Cranage | 137/360 |
| 4,344,455 A | 8/1982 | Norton et al. | |
| 4,619,640 A | 10/1986 | Potolsky et al. | |
| 4,696,326 A * | 9/1987 | Sturgis | 137/614.04 |
| 5,582,166 A | 12/1996 | Lee | |
| 5,682,874 A * | 11/1997 | Grabenkort et al. | 128/200.14 |
| 5,787,879 A | 8/1998 | Gibson | |
| 5,971,972 A | 10/1999 | Rosenbaum | |
| 6,488,026 B2 | 12/2002 | Lauer | |
| 6,508,807 B1 * | 1/2003 | Peters | 604/533 |
| 6,722,705 B2 | 4/2004 | Korkor | |

* cited by examiner

*Primary Examiner* — Nicholas Lucchesi
*Assistant Examiner* — Leah Stohr
(74) *Attorney, Agent, or Firm* — Roylance, Abrams, Berdo & Goodman, L.L.P.

(57) ABSTRACT

A medical air tubing and anti-mismatch fluid distribution system is provided for preventing the inadvertent connection of a feed line to an incorrect source of fluid. The fluid distribution system includes an adapter that is connected permanently to the fluid supply and has an outlet end that is compatible with a coupling member on the feed line. The coupling member on the feed line is compatible with the adapter but is not compatible with the other coupling member of the second fluid supply. A feed line assembly includes a feed line with a connector fixed to a first end and a nebulizer or other medical device fixed to a second end to form a one piece, integrally formed unit. The second fluid supply can include an adapter that is different from the first adapter so that the coupling members of the feed lines are compatible only with the appropriate adapter for the desired fluid source.

12 Claims, 8 Drawing Sheets

MEDICAL AIR TUBING CONNECTION SYSTEM

FIELD OF THE INVENTION

The present invention is directed to a coupling assembly for use in connecting a supply conduit to a supply source. The invention is particularly directed to an anti-mismatch coupling assembly and medical air tube connection system for coupling an air supply tube to an air supply manifold to prevent incorrect connection of the supply tube to the required supply source.

BACKGROUND OF THE INVENTION

Numerous types of couplings have been constructed for coupling a supply conduit to a supply source of a fluid such as a gas or liquid. Many of these couplings are provided with quick disconnect coupling members to enable efficient connection and disconnect from the source.

One example of a fluid supply is commonly used in hospitals and other medical facilities. The supply generally includes a manifold with several outlets for supplying air, oxygen, anesthesia, or other gases. A manifold is often provided in the hospital room which includes at least an oxygen and air supply. The oxygen and air supply typically include a coupling to enable quick and easy coupling of a supply tube to the air or oxygen source to feed air and/or oxygen to the patient through a mask or tube.

One example of a manifold or panel containing a plurality of fluid supplies enables the fluid supply to be connected to different devices. For example, pressure lines from a particular machine can be connected to the manifold and connected to the supply by a quick connect coupling. The coupling mechanism can often include a flow meter or measuring device for measuring the fluid pressure and flow rate.

Care must be taken when connecting a supply conduit to the fluid supply to ensure that the conduit is connected to the correct supply. The supply connections are typically identical so that the feed tube can inadvertently be connected to the incorrect supply. Although the supplies are labeled, errors often occur. There are many instances when the correct fluid is essential to the operation of the equipment or the safety of the patient. For example, in the hospital setting, it is important to ensure the supply of gas being fed to the patient is correctly connected to either the oxygen supply or the air supply as needed. Failure to connect the supply to the proper outlet can result in damage to the instrument or injury to the patient.

Various solutions have been provided to reduce the risk of incorrectly connecting the supply conduit to the outlet. Examples of various solutions have included color codes, labels and non-interchangeable quick connectors.

One example of a quick connect system is disclosed in U.S. Pat. No. 3,170,667 to Szohatsky. The connection system includes a coupling having male and female members that are compatible to enable connection with each other. The system is a non-interchangeable coupling system where the female member includes an external sleeve having a groove that cooperates with the male member. The system also includes a quick connect coupling having a female member with a grooved sleeve mounted externally where the male member includes an external sleeve having a flange mating with the groove sleeve of the female member.

U.S. Pat. No. 4,696,326 to Sturgis discloses an anti-mismatch system for use in fluid conduits where a pair of fluid conduits include matching first and second conduits. The anti-mismatch system prevents the inadvertent connection of mismatched fluid conduits to the source. The anti-mismatch fittings are configured for inter-engagement only with one another and not with anti-mismatch fittings of a different set, thereby enabling connection only of the matching fluid conduits. The fittings are constructed having different axial lengths to prevent mismatch of the couplings to the incorrect fluid supply.

U.S. Pat. No. 4,619,640 to Potolsky et al. discloses a blood transfer connection assembly having a male and female connector. The connectors are constructed to prevent inadvertent connection to an incorrect blood type source. The male connector can include a key or prongs that mate with a corresponding recess in the female connector to ensure proper connection.

U.S. Pat. No. 5,971,972 to Rosenbaum discloses an intravenous infusion system having different connectors for connecting to a particular source. The different connectors prevent mismatch connection to prevent connecting to the improper blood source.

Various other coupling mechanisms have been developed which have a specific shape or dimension to mate with the appropriate coupling member. Examples of such devices are disclosed in U.S. Pat. No. 3,459,177 to Deuschle, U.S. Pat. No. 4,344,455 to Norton et al., U.S. Pat. No. 5,582,166 to Lee, U.S. Pat. No. 5,787,879 to Gibson, U.S. Pat. No. 6,508,807 to Peters, U.S. Pat. No. 6,488,026 to Lauer, and U.S. Pat. No. 6,722,207 to Korkor.

While the prior coupling systems have generally been successful for the intended use, there is a continuing need in the industry for an improved coupling system to prevent mismatch of fluid supplies.

SUMMARY OF THE INVENTION

The present invention is directed to a medical air tubing connection and coupling assembly that prevents mismatch coupling of the supply conduit to the fluid source. The invention is particularly directed to an anti-mismatch coupling system that prevents inadvertent connection of a medical device to the improper supply.

The connector assembly of the present invention can be connected to a standard supply outlet without modification of the outlet. In one embodiment of the invention, the connector assembly of the invention includes an adapter permanently connected to the air supply outlet of a manifold or panel containing a plurality of outlets. A coupling member of a medical device is compatible only with the adapter on the fluid supply and is not compatible with the standard outlet of the manifold or panel. A second supply tube includes a coupling member that is compatible with the standard outlet and is not compatible with the coupling member of the invention. In a preferred embodiment, the adapter is fixed to the air supply in a manner that the adapter is tamper resistant and cannot be removed without damaging the adapter and the fluid supply.

The coupling member of the invention is an adapter that can be coupled directly to the outlet of the fluid supply of a manifold having a plurality of different fluid supply outlets. The adapter is preferably coupled to a fluid outlet to retrofit the existing fluid outlet and is fixed thereto to prevent removal. In one embodiment, the adapter is threaded onto the fluid outlet and is intended to be fixed to the fluid outlet by a locking member such as a set screw. The adapter has an inlet end connected to the supply outlet and an outlet end for connecting to the supply conduit. The outlet end has a shape and/or dimension that is different from the outlet of the manifold. A feed tube has a connector integrally formed therewith that is compatible with the adapter for coupling with the adapter where the coupling is not compatible with the outlet of the manifold. The feed tube has a second end integrally formed with a medical device such as a nebulizer. The second supply conduit is compatible with the outlet of the manifold but is not compatible with the outlet end of the adapter.

Accordingly, one aspect of the invention is to provide a coupling system that allows easy connection to the supply while preventing inadvertent mismatching of the connections.

Another aspect of the invention is to provide a coupling where only compatible male and female members can be connected.

Another aspect of the invention is to provide an anti-mismatch coupling system including an adapter that is permanently fixed to an air supply outlet of a supply manifold.

Another aspect of the invention is to provide a convenient and inexpensive anti-mismatch system that can be used to retrofit an existing supply manifold.

These and other aspects of the invention are basically attained by providing a fluid distribution system comprising a first fluid supply for supply air and having an outlet with a first coupling end, a second fluid supply having an outlet with a second coupling end, and an adapter having a first end with a coupling end that is fixed to the first coupling end of the air supply. The first adapter has a second end with a second coupling end that is incompatible with the first coupling end and the second coupling end. A second adapter is coupled to one of the second fluid supply and has an outlet end with an outwardly facing gripping surface. A first feed assembly has a first connector that is compatible with the second coupling end of the adapter and incompatible with the second coupling end of the second fluid supply. The first feed line is fixed at the first end to the first connector and at a second end to a medical device such as a nebulizer. A second feed line has a second connector that is compatible with the second coupling end of the second fluid supply and is incompatible with the second coupling end of the adapter.

The various aspects of the invention are also attained by providing a fluid distribution system for supplying air and oxygen, comprising a first fluid supply having a first coupling end for supply air, a second fluid supply having a second coupling end for supplying oxygen, and a first adapter coupled to the first coupling ends. The adapter has an axial passage and outlet end with an axial recess defining a coupling member. A first feed assembly has a first connector connected to a first feed line. The first connector has a coupling end that can be removably coupled to the adapter and cannot be coupled to the second coupling member. A nebulizer is fixed to a second end of the first feed line. A second connector is connected to a second feed line. The second connector has a coupling end that is compatible with the second coupling member and incompatible with the first adapter.

The various aspects of the invention are further attained by providing a fluid distribution system for air and oxygen comprising a first fluid supply having an outlet with a first coupling member for supply air, a second fluid supply having an outlet with a second coupling member for supplying oxygen and an adapter having a first end with a first coupling member for mating with the first coupling member of the first supply and having a second end with a female coupling member. A second adapter has a first end with a first coupling member for mating with the second coupling member of the second fluid supply in a second end with a male coupling member. The system includes a first feed assembly having a male connector for mating with the female connector of the first adapter, a medical device and a feed tube fixed to the connector and the medical device. A second feed line has a female connector for mating with the male connector of the second adapter.

These and other aspects of the invention will become apparent from the following detailed description of the invention which in conjunction with the annexed drawings, disclose various embodiments of the invention.

BRIEF DESCRIPTION OF THE DRAWINGS

The following is a brief description of the drawings, in which.

DETAILED DESCRIPTION OF THE INVENTION

The present invention is directed to an air tubing connection and fluid distribution system that prevents improper connection to a fluid source. The invention is particularly directed to a fluid distribution system that prevents mismatching of coupling members to reduce or eliminate the risk of inadvertently connecting a feed line to an incorrect fluid supply.

The fluid distribution system of the invention is suitable for use with a supply manifold or panel having a plurality of supply outlets that are able to supply a fluid and particularly a gas such as air and oxygen. The distribution system of the invention is suitable for use with a variety of fluids including liquids and gases. In the illustrated embodiment, the fluid distribution system is disclosed in connection with a supply of air and oxygen. In one preferred embodiment of the invention, the gases are oxygen and/or air that are typically supplied in a hospital or other medical facility. The fluid distribution system of the invention prevents the inadvertent connection of the oxygen supply to an air feed line and prevents connection of the air supply to an oxygen feed line.

Figure 1:
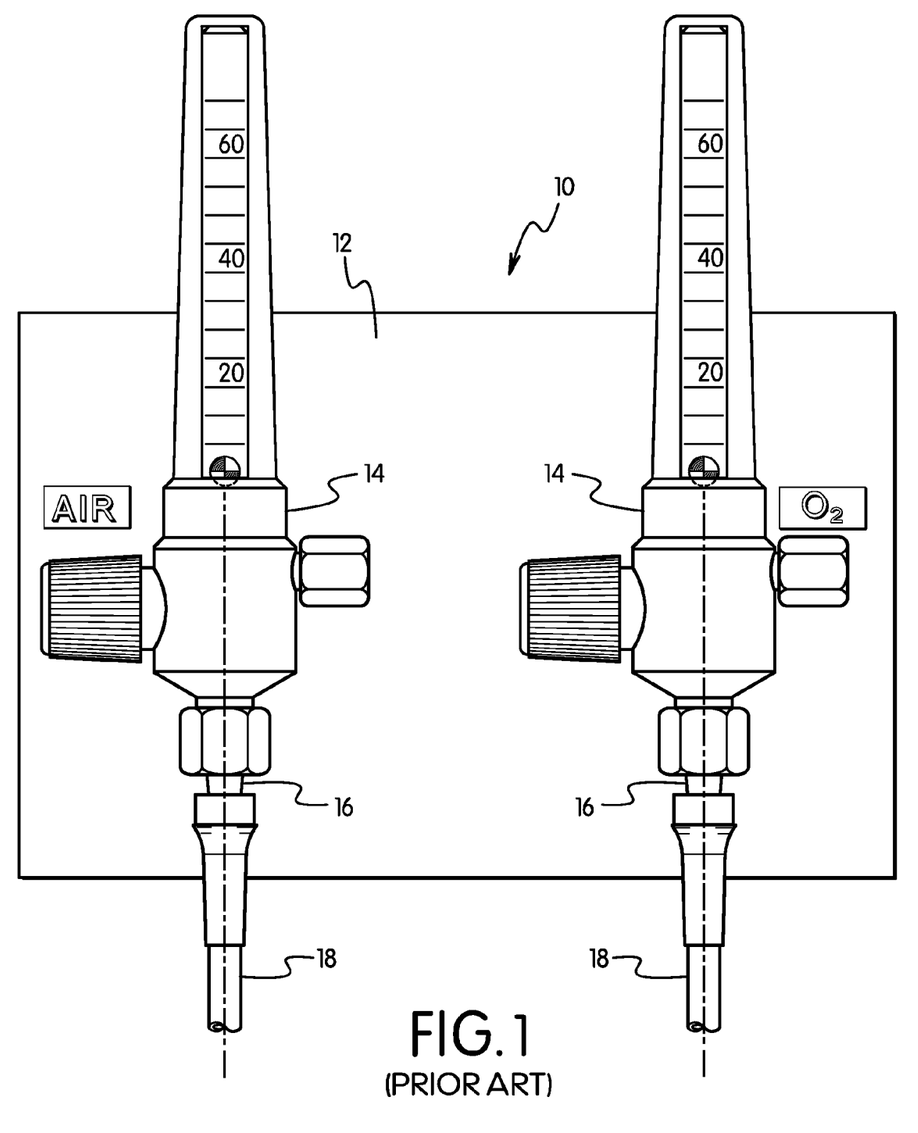
FIG. 1 is an elevational view of a conventional supply manifold and outlet.

A typical supply system commonly used in hospitals and medical facilities is shown in FIG. 1. The supply system 10 includes a panel 12 with a plurality of outlets having a flow meter 14 connected to each outlet. A coupling nipple 16 is connected to each of the oxygen and air supplies for connecting with a supply tube 18. As shown in FIG. 1, the conventional system provides interchangeable nipples 16 and tubes 18 such that each tube can be connected to either nipple thereby creating a significant risk of inadvertently connecting the tube 18 to the incorrect air or oxygen source.

Figure 2:
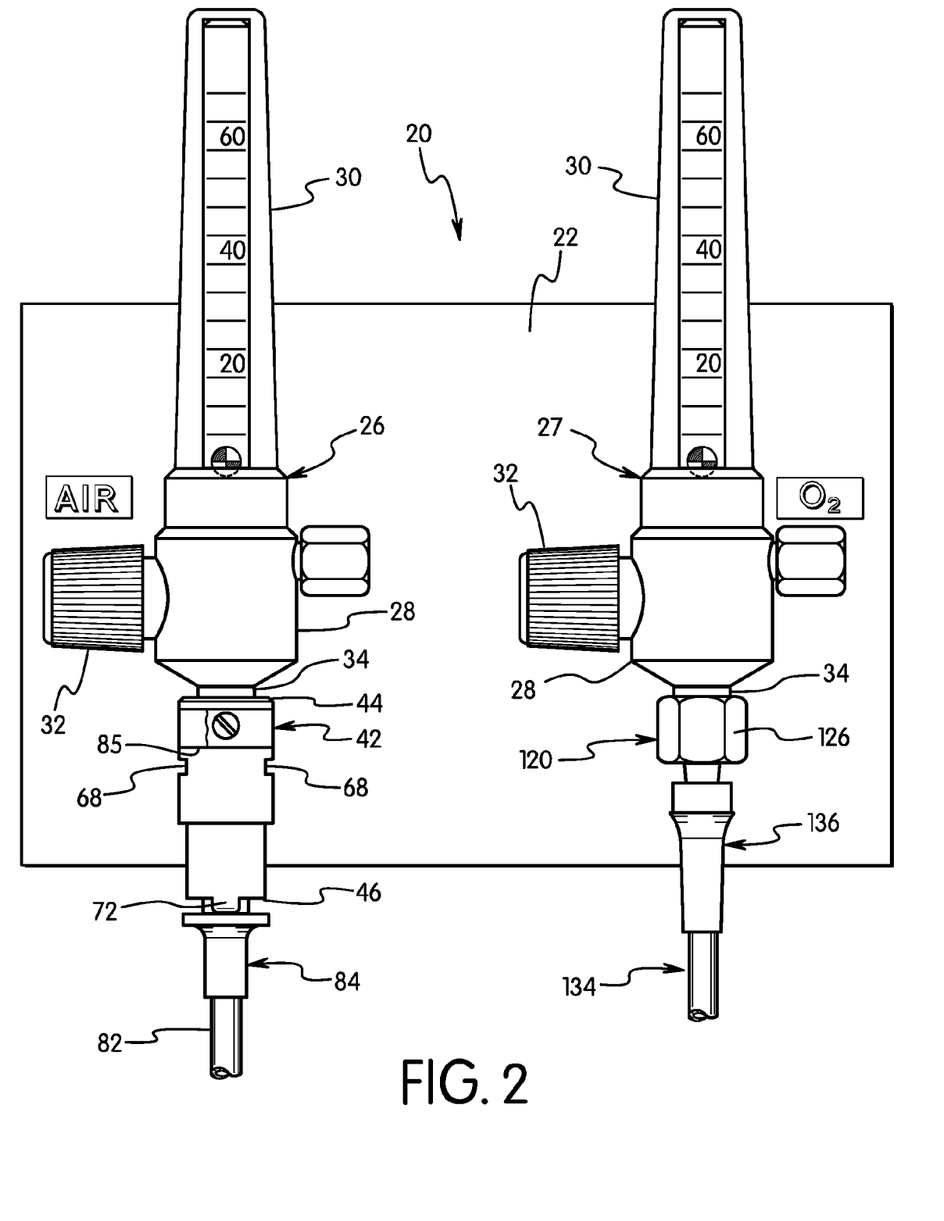
FIG. 2 is an elevational view of the fluid distribution system of the invention according to one embodiment.
Figure 3:
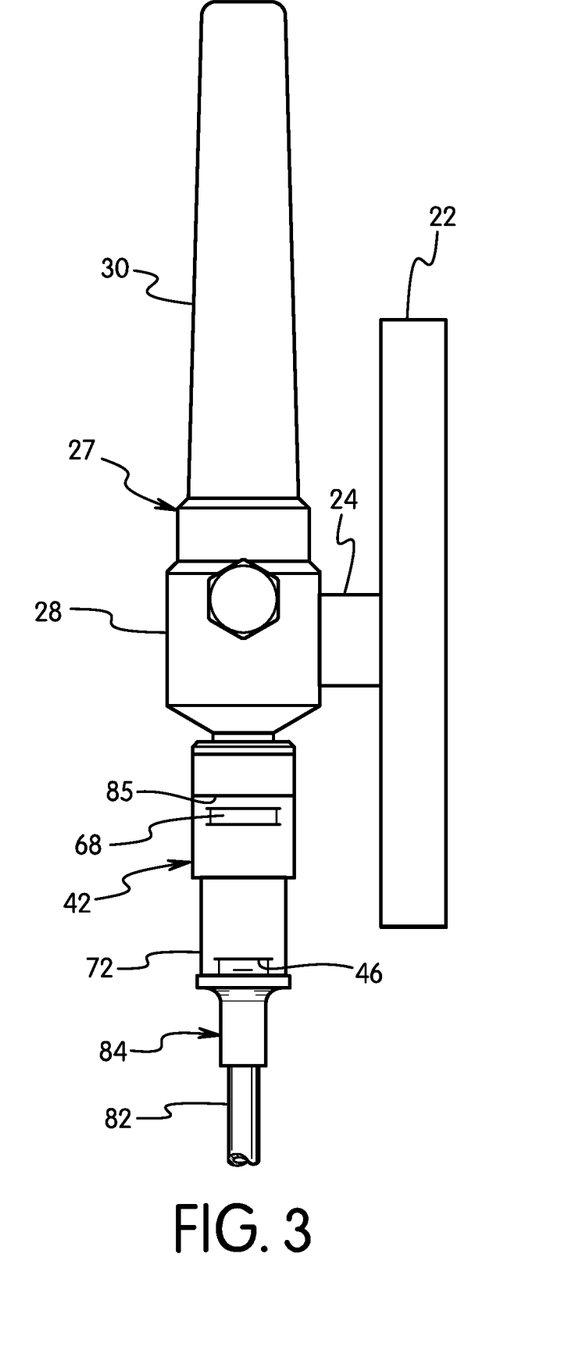
FIG. 3 is a side view of the fluid distribution system of FIG. 2.

Referring to FIGS. 2 and 3, the fluid distribution system 20 of the invention includes a distribution manifold 22 shown as a panel having a plurality of fluid outlets 24. Fluid outlets 24 typically include a threaded coupling end for connecting to a valve or other distribution system. In the embodiment illustrated, each outlet 24 is connected to flow meters 26 and 27 to control the flow rate and pressure of the fluid being supplied. The flow control meter 26 and 27 are typically threaded onto the threaded end of the outlet 24.

The manifold 22 supplies a variety of different gases depending on the utility of the manifold. In one embodiment of the invention, manifold 22 provides a source of oxygen and a source of air. In other embodiments of the invention, different gases can also be supplied, such as nitrogen.

Figure 4:
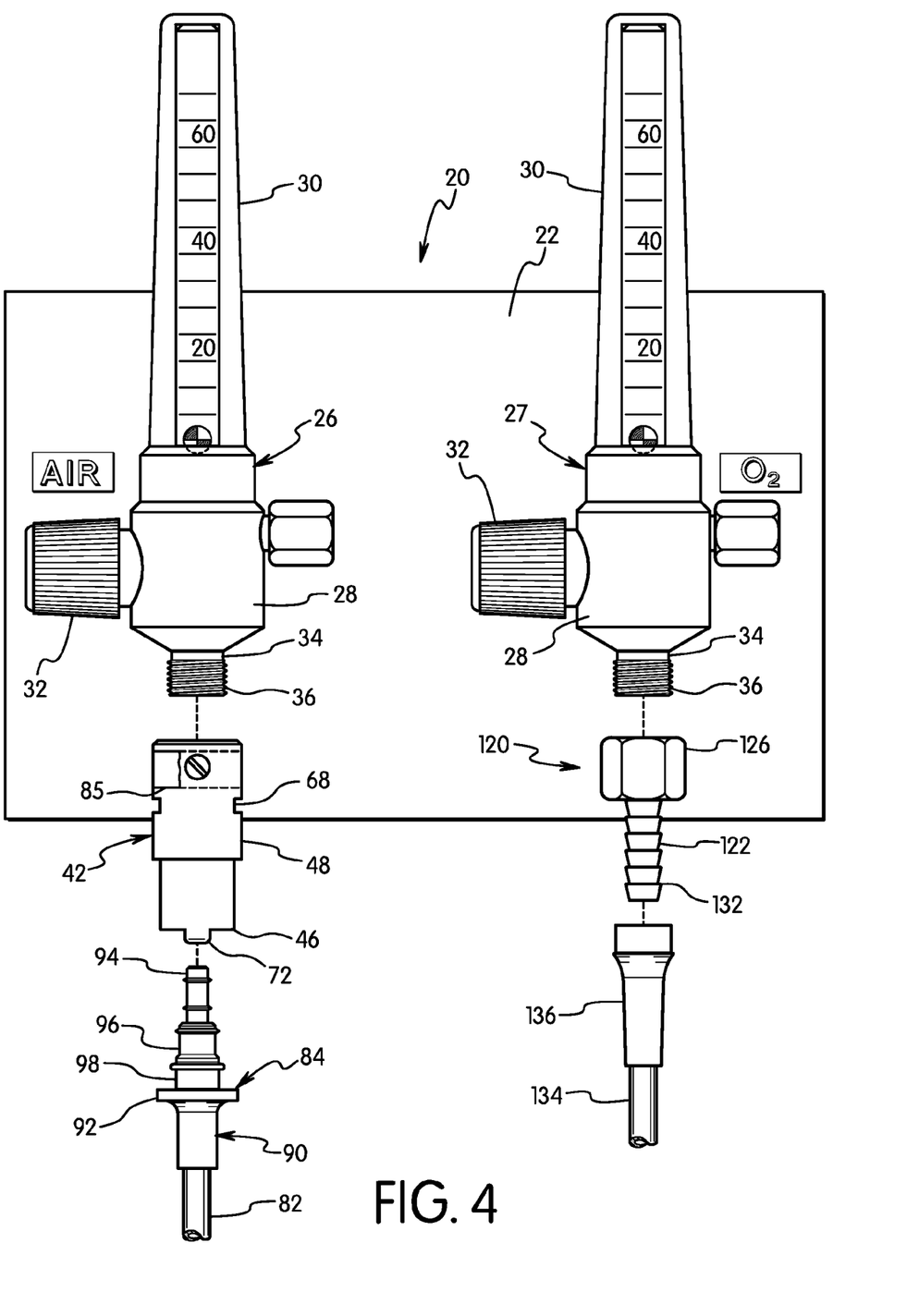
FIG. 4 is an exploded elevational view of the fluid distribution system of FIG. 2.
Figure 5:
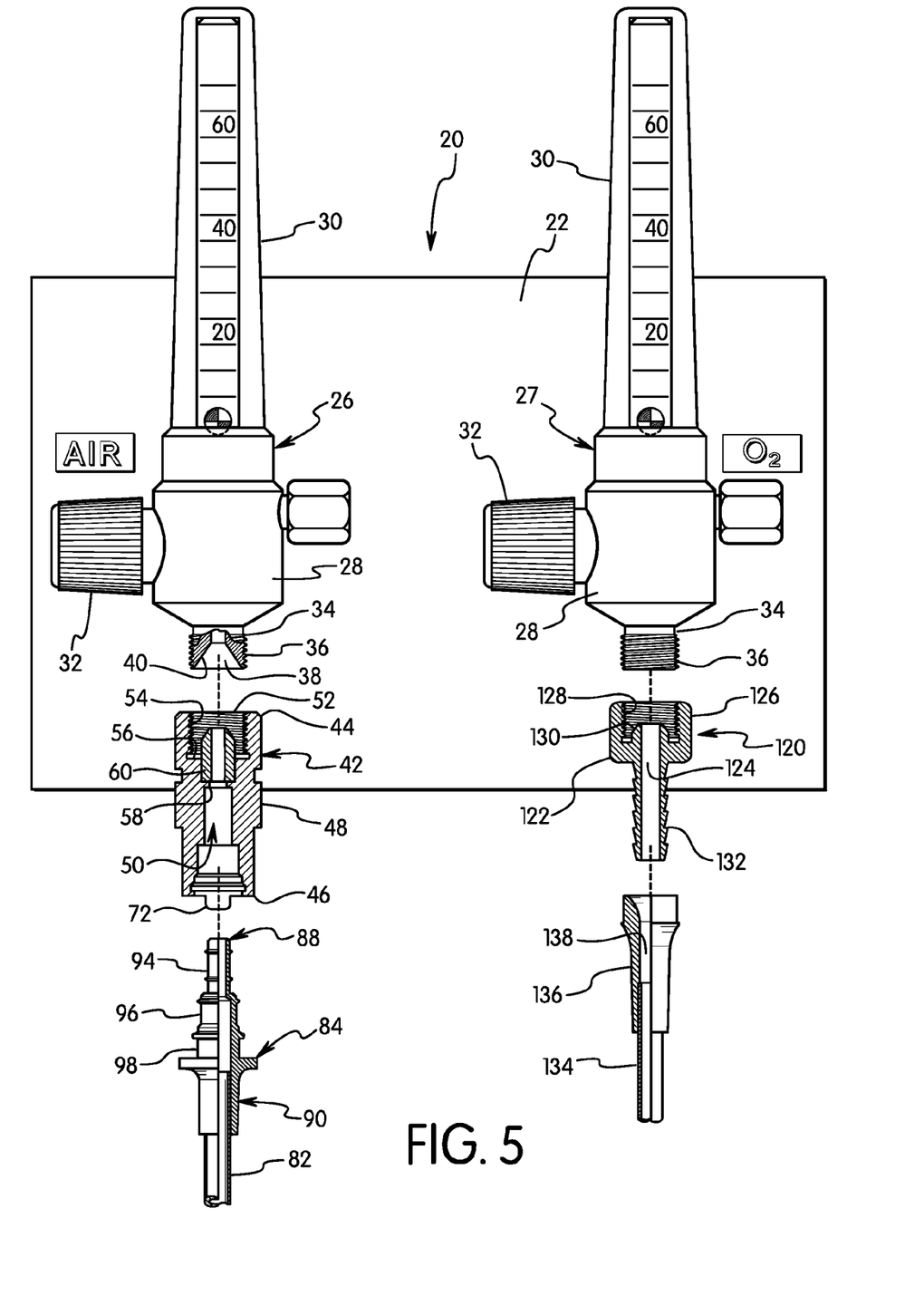
FIG. 5 is an exploded elevational view in partial cross-section of the fluid distribution system of FIG. 2.

Flow meters 26 and 27 in the illustrated embodiment are shown as being connected to an oxygen and air supply, respectively. Each flow meter is substantially identical so that the parts are identified by the same reference number. Referring to FIGS. 2, 3 and 4, flow meters 26 and 27 includes a main body 28 connected to outlet 24 of manifold 22. A gauge 30 extends upwardly from main body 28 to display the pressure and flow rate of gas passing through flow meter 26. An adjustment valve 32 in main body 28 is used to adjust the flow rate and pressure. The threaded outlet 34 extends from main body 28 to dispense the gas to the desired source. Outlet 34 in the embodiment illustrated includes external threads 36 and an axial passage 38 as shown in FIG. 5. As shown in FIG. 5, axial passage 38 includes an internal frustoconical sealing surface 40 capable of mating with a coupling member.

A first adapter 42 is coupled to the outlet 34 of flow meter 26. Adapter 42 has an inlet end 44 and an outlet end 46. Adapter 42 in the embodiment illustrated has a substantially smooth cylindrical outer surface 48 and an axial passage 50 extending between inlet end 44 and outlet end 46.

As shown in FIG. 5, inlet end 44 of adapter 42 defines a recessed portion 52 and threaded inner walls 54. Recessed portion 52 has a dimension to be coupled to outlet 34 by the corresponding threads 36 and 54. In one embodiment of the invention, inlet end 54 of adapter 42 is compatible with each of the outlets 34 of the flow meters 26 so that adapter 42 can be coupled selectively to either one of the flow meters. In the embodiment illustrated, adapter 42 is coupled to the flow meter for supplying air.

Figure 7:
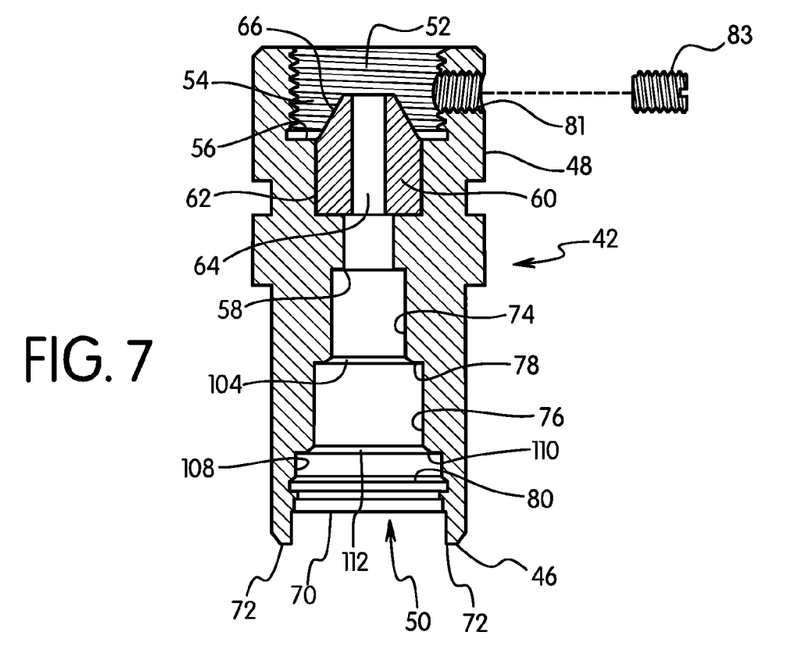
FIG. 7 is a cross-sectional view of the adapter in the embodiment of FIG. 2.

Recessed portion 52 of adapter 42 has a bottom wall 56 encircling axial passage 50 as shown in FIG. 5. Axial passage 50 includes an inwardly extending annular flange 58 for supporting a seal 60. As shown in FIGS. 5 and 7, seal 60 has a cylindrical side wall 62, an axial passage 64, and a frustoconical top end 66 for mating with the sealing surface 40 of outlet 34.

Adapter 42 is generally made of a rigid material such as stainless steel, although other materials can also be used. Seal 60 is generally a softer material capable of forming a fluidtight seal against sealing surface 40 when compressed against sealing surface 40. Seal 60 can be made of a metal such as brass or a polymeric material such as nylon. Adapter 42 in the embodiment illustrated includes flat planar recesses 68 in the outer side wall for receiving a wrench or other tool to tighten adapter 42 onto outlet 34 with sufficient force to axially compress seal 60 and form a fluidtight seal between outlet 34 and adapter 42.

Outlet end 46 of adapter 42 includes an axial face with a pair of axially extending tabs 72. Axial passage 50 at outlet end 46 defines a first inner cylindrical section 74 and a second inner cylindrical section 76 separated by a step 78. As shown in FIGS. 5 and 7, first cylindrical section 74 has a diameter less than the diameter of second cylindrical section 76. The axial end of second cylindrical section 76 includes two stepped portions 80 with progressively larger internal diameters.

Inlet end 54 of adapter 42 includes a threaded bore 81 for receiving a threaded screw 83. Threaded bore 81 extends radially through the side of adapter 42 into recessed portion 52. Threaded bore 81 is oriented to align with the threaded outlet 36 of the flow meter 26. In a preferred embodiment of the invention, adapter 42 is threaded onto the threaded end of the flow meter and the screw 83 is tightened to bite into the threaded end of the flow meter to secure the adapter permanently to the flow meter. In this manner, the adapter cannot be removed without great effort and without damaging the threads and/or the adapter. Preferably, the head of the screw 83 is recessed or flush with the outer surface of the adapter so as not to be readily accessible, thereby inhibiting tampering. In one preferred embodiment, a label 85 or other covering is applied over the screw head so that the screw is not visible under normal use. The label or cover deters tampering by obscuring the screw and provides evidence of tampering in the event an attempt is made to remove the adapter. In the embodiment shown, screw 83 provides a locking system to attach the adapter permanently to the flow meter. In other embodiments, other locking members can be used that are capable of preventing or inhibiting the removal of the adapter from the flow meter.

A first fluid feed line 82 includes a coupling member 84 for coupling with adapter 42. First fluid feed line 82 is typically a flexible plastic tubing that leads to a nebulizer, mask, hood or other medical device for supplying air to a patient. In the preferred embodiment of the invention, feed line 82 is preferably fixed permanently to coupling member 84 for easy connection to adapter 42.

Figure 5A:
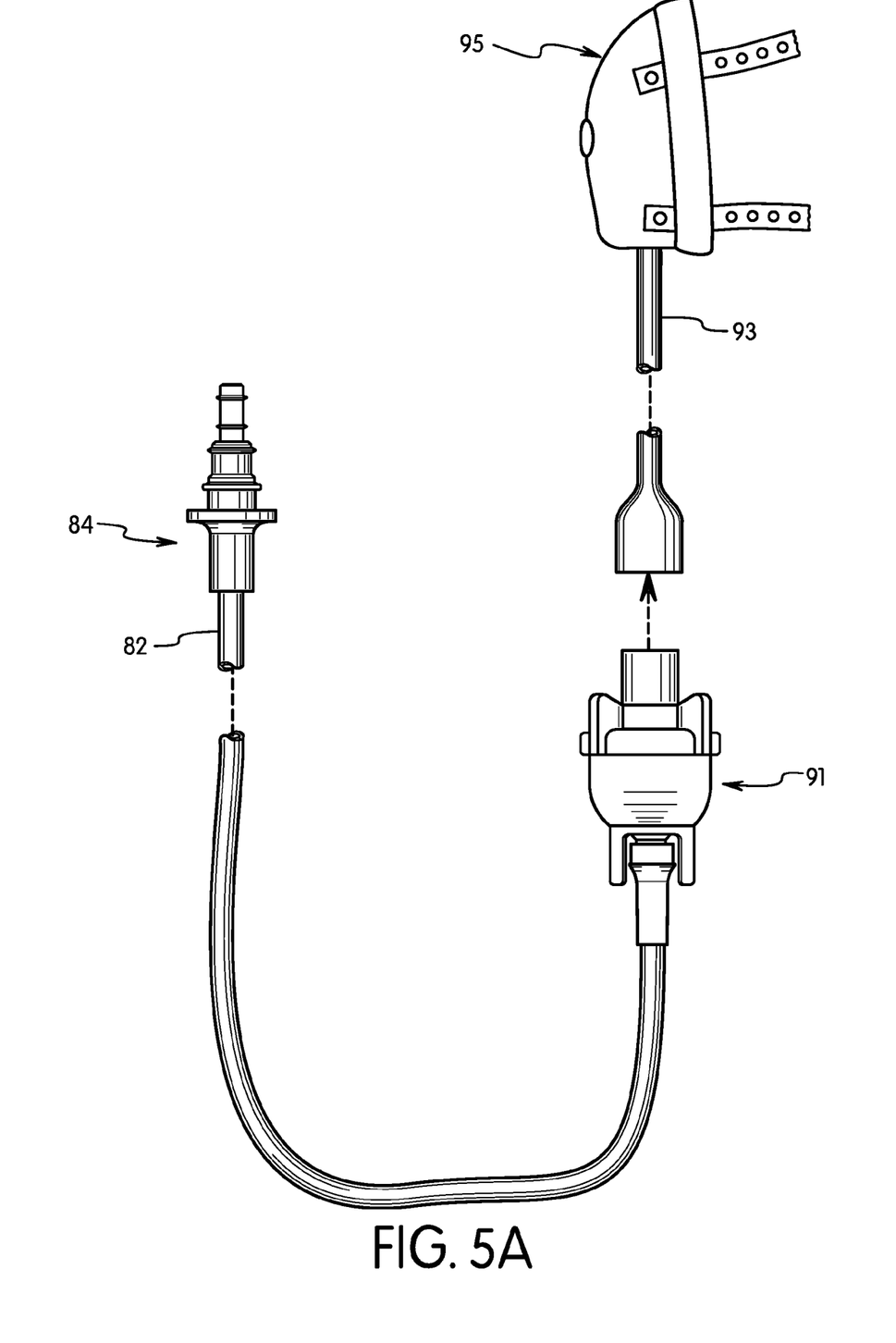
FIG. 5A is an elevational view of the feed assembly showing the coupling member, feed tubes, nebulizer and mask.
Figure 6:
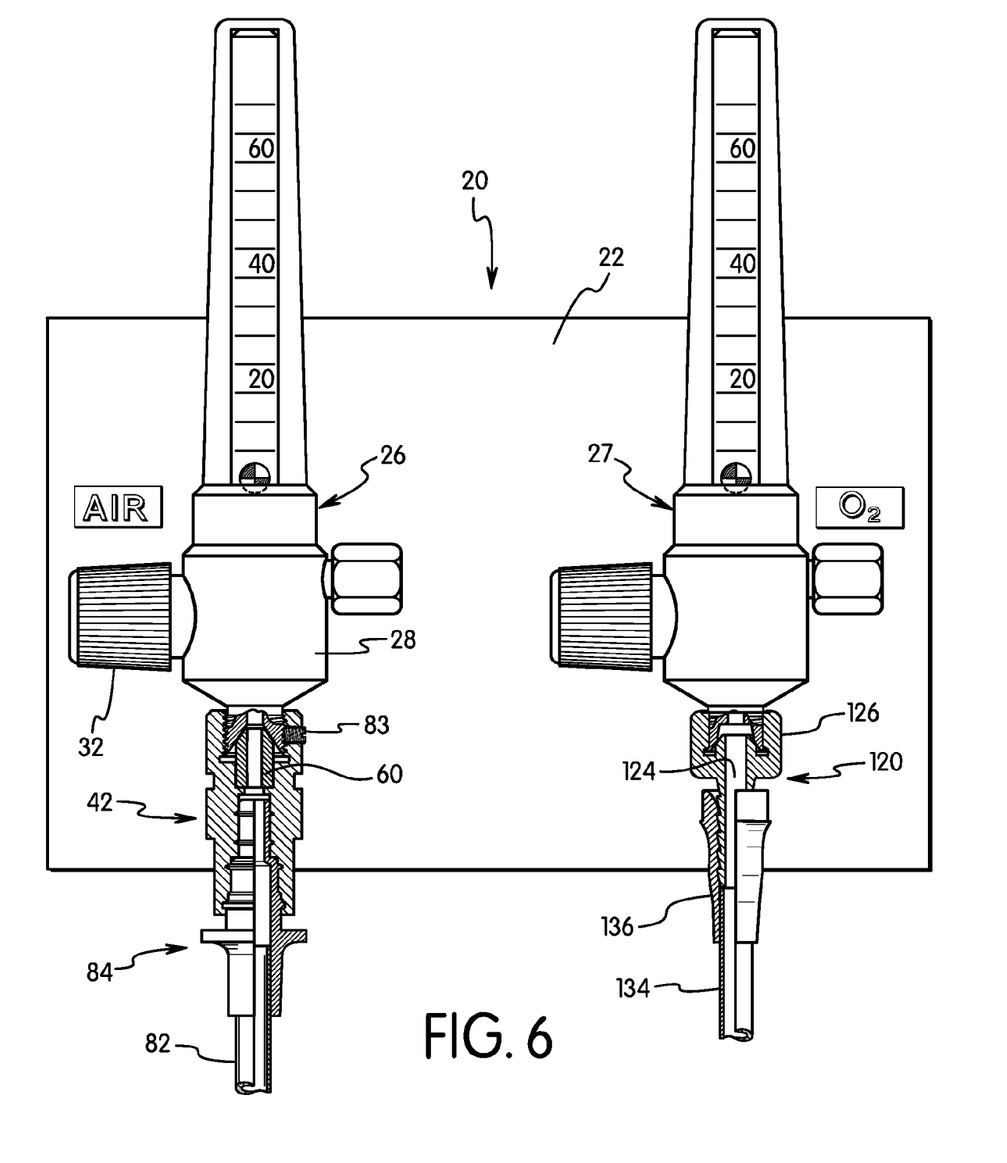
FIG. 6 is an elevational view in partial cross-section of the fluid distribution system of FIG. 2.

The fluid distribution system in a preferred embodiment provides an adapter coupled to an air supply where the adapter coupling is permanently attached to the air supply outlet. In a preferred embodiment, a nebulizer 91 is permanently fixed to one end of the feed line 82 that serves as a supply tube. The coupling member 84 is able to mate with the adapter 42 only so that the medical device cannot be inadvertently connected to an incorrect fluid supply. The medical device such as the nebulizer 91, supply tubing 82 and coupling member 84 form a one piece integral feed assembly for the air. Preferably, the coupling member and nebulizer are fused to the tube 82 and cannot be separated without damaging or destroying the feed assembly, the adapter and the nebulizer.

Figure 8:
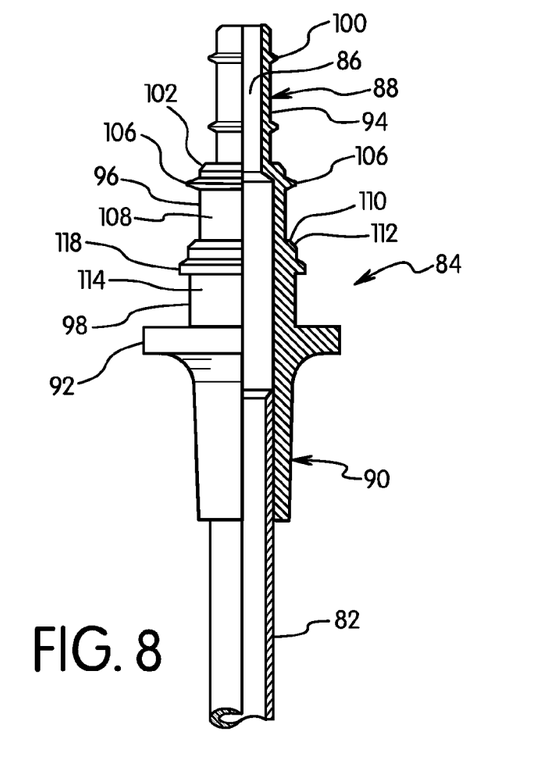
FIG. 8 is a partial cross-sectional elevational view of the coupling member for mating with the adapter.

As shown in FIGS. 5 and 8, coupling member 84 has a shape and dimension that is compatible with the recess in the outlet end 46 of adapter 42. In the embodiment illustrated, outlet end 46 of adapter 42 defines a female end and the coupling member 84 of feed line 82 defines a male member for coupling with adapter 42. Coupling member 84 is preferably a unitary one piece member made of rigid but resilient plastic material that is able to form a fluidtight seal with the adapter.

Coupling member 84 has a longitudinal dimension with an axial passage 86, a coupling end 88 and a base 90. Base 90 has a substantially cylindrical shape with an open end fixed to feed line 82. Preferably, base 90 is permanently fixed to feed line 82 by welding, the use of adhesive or other coupling means that prevents separation of the coupling member from feed line 82 without damaging the assembly and rendering the assembly inoperable. Base 90 has a collar 92 that extends radially outward from base 90.

In a preferred embodiment of the invention, the first feed line 82 has a first end fixed to coupling member 84 and second end fixed to the nebulizer 91. The coupling member 84, feed line 82 and nebulizer 91 form a one piece, integrally formed unit where the coupling member and nebulizer cannot be separated. The nebulizer 91 can be connected to a tube 93 which is connected to a mask 95. In one embodiment, the mask 95 and tube can be permanently fused to the nebulizer to form a one piece unit. Nebulizer 91 functions in a conventional manner to supply a medicament to a patient through a mask by vaporizing the medicament. The nebulizer has a construction similar to conventional nebulizers. Fixing the feed line 82 and coupling member 84 to the nebulizer or other medical device prevents the assembly from being coupled to a non-specific or universal coupling member and prevents inadvertently coupling to an oxygen or other fluid supply. Providing a unitary assembly of the nebulizer, tube and coupling member and an adapter that mates only with the coupling member of the unitary assembly, reduces or substantially eliminates the risk of inadvertently connecting the nebulizer to the oxygen supply.

Coupling end 88 of adapter 84 has a cylindrical distal portion 94, an intermediate portion 96, and a cylindrical base portion 98. Distal portion 94 has a cylindrical shape with an axial length complementing the axial length of first inner cylindrical section 74 of adapter 42. Distal portion 94 has an outer diameter that is compatible with the inner diameter of first cylindrical section 74 to form a seal therebetween. The outer surface of distal portion 94 is provided with at least one annular rib 100 extending radially outward to contact the inner surface of first cylindrical section 74 and form a fluidtight seal. As shown, two axially spaced apart ribs 100 are provided, although any number of ribs can be provided.

Intermediate portion 96 of coupling 84 has a frustoconical outer end 102. As shown in FIG. 7, the step 78 includes a frustoconical inner edge 104 for mating with the frustoconical end 102 of intermediate portion 96. Intermediate portion 96 has a substantially cylindrical shape with at least one outwardly extending sealing rib 106. Rib 106 preferably extends radially outward a distance to contact the inner surface of the second inner cylindrical section 76 of adapter 42. Intermediate section 96 preferably has an axial length corresponding substantially to the axial length of cylindrical section 76 and has an outer diameter complementing the inner diameter of cylindrical section 76 to form a fluidtight seal.

As shown in FIG. 7, the cylindrical section 76 of adapter 42 has an inner diameter less than the inner diameter of the axial passage at the outlet end 46. A cylindrical section 108 is formed at the outlet end 46 of adapter 42 and is separated from the cylindrical section 76 by a step 110. Step 110 includes a frustoconical shaped portion 112.

Base portion 98 of coupling member 84 includes a cylindrical outer surface 114 with a frustoconical end 116 and an annular rib 118. Annular rib 118 extends radially outward from outer surface 114. Frustoconical shaped end 116 has a shape and dimension compatible with the frustoconical portion 112 of step 110 to mate together and form a sealing surface. Rib 118 has an outer dimension complementing the inner dimension of steps 80 of adapter 42 to form a seal.

Coupling member 84 is preferably a one piece integrally formed member. Coupling member 84 is preferably made of a plastic material having a resilience sufficient to couple to adapter 42 and form a fluidtight sealing surface. In one embodiment of the invention, coupling member 84 is made of a thermoplastic elastomer (TPE).

As shown in FIG. 2, a second adapter 120 is connected to flow meter 27 for supplying a different fluid from flow meter 26. Adapter 120 is preferably made of a rigid material such as metal or plastic. Preferably, the second adapter 120 is connected to one fluid supply while the adapter 42 is connected to the other fluid supply. Adapter 120 has a body 122 with an axial passage 124. A collar 126 having internal threads 128 is provided for coupling with the external threads on the outlet 34 of the flow meter 27. The axial end of body 122 has a frustoconical edge 130 for mating with the frustoconical surface of the outlet of the flow meter for forming a seal. The outer surface of body 122 includes angled outwardly extending ribs 132 or barbs. A feed line 134 includes a coupling member 136 having an axial passage 138 with an internal dimension complementing the outer dimension of body 122 of adapter 120. Coupling member 136 is pressed onto the body 122 to couple the feed line 134 to adapter 120. Ribs 132 grip the inner surface of coupling member 136. Coupling member 136 is preferably made from a resilient plastic material that is able to grip adapter 120 and form a fluidtight seal.

The distribution system of the invention prevents the inadvertent connection of a feed tube to the incorrect fluid supply and ensures proper connection of the feed line to the correct fluid supply. In the embodiment illustrated in the invention, flow meters provide a source of oxygen and a source of air. The adapter for the air supply is permanently connected to the flow meter of the air supply so that the feed lines can be connected only to the appropriate source. In the embodiment illustrated, adapter 42 is coupled to the air supply and flow meter 26. Adapter 42 includes a female inlet end that is connected to the outlet of the flow meter and includes a female outlet end that is able to mate only to coupling 84. The adapter 120 includes a female inlet end coupled to the outlet of the flow meter 27 and includes a male outlet end that is able to mate only with coupling 136. Thus, the outlet ends of the adapters 42 and 120 are not compatible and the feed lines are not interchangeable. The feed line for the oxygen supply is provided with the coupling member 84 that is not compatible with adapter 42. Thus, the feed line for the air supply cannot be inadvertently connected to the oxygen supply. In the same manner, the feed line for the oxygen is coupled to the coupling member 136 which can only be coupled to the end of the adapter 120. The coupling member 136 is not compatible with the end of the adapter 48 so that the oxygen feed line cannot be inadvertently connected to the oxygen supply.

While various embodiments have been chosen to illustrate the invention, it will be understood by those skilled in the art that various changes and modifications can be made without departing from the scope of the invention as defined in the appended claims.

What is claimed is:

1. A fluid distribution system for supplying air and oxygen, comprising:
   a first fluid supply having a first coupling end for supplying air, said first coupling end of said first fluid supply having external threads;
   a second fluid supply having a second coupling end for supplying oxygen;
   a first adapter coupled to said first coupling end of said first fluid supply, said first adapter having an axial passage, an outlet end with an axial recess defining a coupling member, and a locking member to fix said first adapter permanently to said first fluid supply, said axial passage of said first adapter having internal threads for mating with said external threads, said first adapter having a radial bore communicating with said axial passage and a threaded screw received in said radial bore to engage said external threads to fix said first adapter permanently to said first fluid supply and a tamper indicator overlying said radial bore to detect tampering with said first coupling member;
   a second adapter coupled to said second coupling end, said second adapter having an outlet end with an outer surface defining a coupling member;
   a first feed assembly including a first connector fixed permanently to a first feed line and having a coupling end with an outer coupling surface that can be removably coupled to said first adapter and is incompatible with said second adapter, and a nebulizer fixed permanently to a second end of said first feed line, said first feed assembly being a one piece integrally formed unit; and a second connector connected to a second feed line and having a coupling end with an inner coupling surface that is compatible with said outer surface of said second adapter and incompatible with said first adapter.

2. The fluid distribution system of claim 1, wherein said first adapter has a substantially cylindrical outer surface, a radially extending bore communicating with said axial passage, and a threaded screw received in said bore and engaging said first fluid supply to permanently fix said first adapter to said first fluid supply.

3. The fluid distribution system of claim 1, wherein said first adapter has a first end with a first coupling that is compatible with said first coupling end of said first fluid supply, and a second end that is compatible with said first connector and incompatible with said second connector.

4. The fluid distribution system of claim 1, wherein said first end of said first adapter has a female coupling for coupling with said first fluid supply and said second end has a female coupling for receiving said first connector of said first feed assembly.

5. The fluid distribution system of claim 1, wherein said outlet end of said second adapter defines a male end; and said coupling end of said second connector defines a female coupling to said first connector.

6. The fluid distribution system of claim 1, wherein said second connector is made of a resilient material and has an open axial end with a dimension to couple with said coupling member of said second adapter, and where said coupling member of said second adapter has outwardly extending barbs to grip said second connector.

7. The fluid distribution system of claim 1, wherein said female coupling of said first adapter has a cylindrical inner wall; and said first connector has a plurality of annular sealing ribs extending radially outward for mating with said cylindrical inner wall.

8. A fluid distribution system for supplying oxygen and air, said system comprising:

a first fluid supply having an outlet with a first coupling with external threads for supplying air;

a second fluid supply having an outlet with a second coupling for supplying oxygen;

a first adapter having a first end with a first tamper resistant coupling member fixed to said first coupling of said first fluid supply to prevent separation of said first adapter from said first fluid supply, and a second end having a female coupling member, said first adapter having an axial passage with internal threads for mating with said external threads of said first coupling, a radial bore communicating with said axial passage and receiving a threaded screw to engage said external threads to fix said first adapter permanently to said first fluid supply, and a tamper indicator overlying said radial bore to detect tampering with said first adapter;

a second adapter having a first end with a first coupling member coupled to said second coupling of said second fluid supply, and a second end with a male coupling member;

a first feed line having a male connector for mating with said female connector of said first adapter, said male connector being fused to a first end of said first feed line and a medical device fused to a second end of said first feed line; and a second feed line having a female connector for mating with said male connector of said second adapter.

9. The fluid distribution system of claim 8, wherein said first fluid supply includes a flow meter and where said first adapter is connected to said flow meter by said first coupling; and said second fluid supply includes a flow meter and where said second adapter is connected to said flow meter by said second coupling.

10. The fluid distribution system of claim 8, wherein said first end of said first adapter is a female coupling that is compatible with said first coupling; and said first end of said second adapter is a female coupling that is compatible with said second coupling.

11. The fluid distribution system of claim 8, wherein said female coupling of said first adapter has a cylindrical inner wall; and said male connector of said first feed line has a plurality of annular sealing ribs extending radially outward.

12. The fluid distribution system of claim 8, wherein said medical device includes a nebulizer having an inlet end fixed to said first feed line and an outlet end coupled to a mask.

* * * * *